United States Patent [19]

Knaus et al.

[11] Patent Number: 4,937,308

[45] Date of Patent: Jun. 26, 1990

[54] PREPARATION OF ALKYL O,O-DIALKYL-γ-PHOSPHONOTIGLATES

[75] Inventors: Guenter H. Knaus, Ludwigshafen; Hansgeorg Ernst, Speyer; Marco Thyes, Ludwigshafen; Joachim Paust, Neuhofen, all of Fed. Rep. of Germany

[73] Assignee: BASF Aktiengesellschaft, Ludwigshafen, Fed. Rep. of Germany

[21] Appl. No.: 205,283

[22] Filed: Jun. 10, 1988

[30] Foreign Application Priority Data

Jun. 12, 1987 [DE] Fed. Rep. of Germany ....... 3719622

[51] Int. Cl.[5] .............................................. C07F 9/40
[52] U.S. Cl. ................................................. 558/124
[58] Field of Search ........................................ 558/124

[56] References Cited

U.S. PATENT DOCUMENTS 4,424,369 1/1984 Schmidt .............................. 549/273
4,543,417 9/1985 Schmieder et al. ................. 549/375

FOREIGN PATENT DOCUMENTS 031932 12/1980 European Pat. Off. .
110329 2/1986 European Pat. Off. .
3244272 5/1984 Fed. Rep. of Germany .

OTHER PUBLICATIONS

Houben–Weyl, *Methoden des Organischen Chemic*, 12/1 (1963), pp. 434, & 435.
Houben–Weyl, *Methoden des Organischen Chemie*, 5/1 d, p. 128.
*Journal of The Chemical Society*, Part II, 1968, p. 1991.
Cookson et al., "Tetracyanocyclopentadienide Anion and Its Electrophilic Aromatic Substitution", *Journal of The Chemical Society*, 1966, p. 2163.
Houben–Weyle, *Methoden des Organischen Chemie*, 5/1 d (1972), p. 129.
Pattenden et al., "Carotenoids and Related Compounds. Part XIX. The Geometrical Isomers of 2- and 3-Methyl-5-phenylpenta-2,4-dienoic Acid and their Methyl Esters", *Journal of the Chemical Society*, 1968, pp. 1997–2006.

*Primary Examiner*—Anton H. Sutto

*Attorney, Agent, or Firm*—Oblon, Spivak, McClelland, Maier & Neustadt

[57] ABSTRACT

Alkyl γ-halotiglates of the general formula I

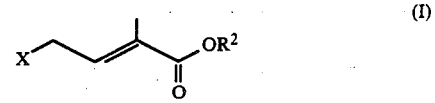

where X is Cl or Br and $R^2$ is alkyl of 1 to 3 carbon atoms, having a high E isomer content, are prepared by a process in which (a) the corresponding 2-methyl-but-3-enoate of the general formula II

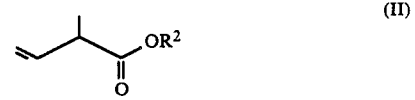

is reacted with chlorine or bromine in the absence of a solvent and (b) the resulting 2-methyl-3,4-dihalobutyrate of the general formula III pt,0012
is dehydrohalogenated by reaction with a solution of an alkali metal hydroxide in an alcohol $R^2OH$, where $R^2$ has the stated meaning, or in a mixture of water and an alcohol $R^2OH$, and the products are further processed to give O,O-dialkyl-γ-phosphonotiglates of the general formula IV

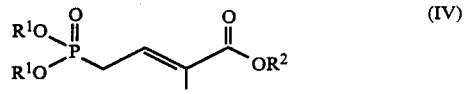

where $R^1$ is alkyl of 1 to 4 carbon atoms and $R^2$ is alkyl of 1 to 3 carbon atoms, preferably ethyl, by reaction with a trialkyl phosphite and thermal isomerization. The process gives $C_5$ building blocks which are extremely interesting for polyene chemistry, the said building blocks being obtained in good yields and essentially in the form of the required E isomers.

5 Claims, No Drawings

PREPARATION OF ALKYL O,O-DIALKYL-γ-PHOSPHONOTIGLATES

γ-Halotiglates, in the form of the corresponding Wittig reagents (3-alkoxycarbonylbut-2-en-1-yltriphenylphosphonium halides), are required as $C_5$ building blocks in polyene chemistry, for example for the preparation of β-apo-8'-carotenates (cf. German Laid-Open Application DOS 3,244,272). For the synthesis of the ethyl β-apo-8'-carotenates described in the above publication, the ethyl γ-halotiglates are of particular interest.

EP-A-110 329 discloses a process for the preparation of γ-chloro- and γ-bromotiglates of lower alcohols. The important intermediates in this process are the 2-methylbut-3-enoates of the general formula II (referred to here as α-vinylpropionates), which are converted into the 2-methyl-3,4-dihalobutyrates of the general formula III by addition of chlorine or bromine. By dehydrohalogenation, these are converted into the γ-halotiglates of the general formula I

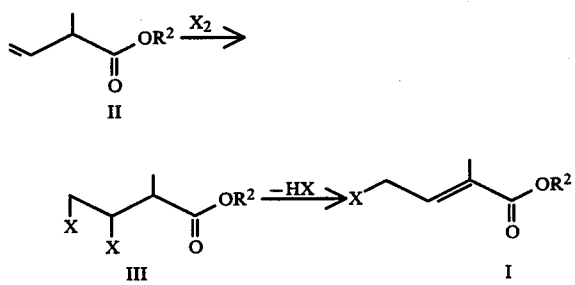

(where X is Cl or Br and $R^2$ is alkyl).

This process, which in principle is advantageous, gives rise to problems when carried out on an industrial scale. For example, the halogenation is carried out, in the usual manner, in chlorohydrocarbons as solvents, which is disadvantageous for process engineering reasons (expensive solvent recycling) and ecological reasons (toxicity of the chlorohydrocarbons). Moreover, the dehydrohalogenation is carried out with alkali metal alcoholates, with the result that the costs of the materials used are very high and the procedure is made more difficult because water has to be excluded.

We have found, surprisingly, that the problems encountered when converting to the industrial scale can be solvent in an elegant manner by (a) carrying out the halogenation in the absence of solvents and
(b) effecting the dehydrohalogenation not with an alkali metal alcoholate but with an alkali metal hydroxide in a lower alcohol or even in water to which a lower alcohol has been added as a solubilizer.

The present invention therefore relates to a process for the preparation of alkyl γ-halotiglates of the general formula I

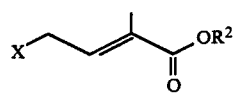

(I)

where X is Cl or Br and $R^2$ is alkyl of 1 to 3 carbon atoms, preferably ethyl, wherein (a) the corresponding 2-methylbut-3-enoate of the general formula II

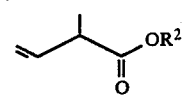

(II)

where $R^2$ has the above meaning, is reacted with chlorine or bromine in the absence of a solvent and
(b) the resulting 2-methyl-3,4-dihalobutyrate of the general formula III

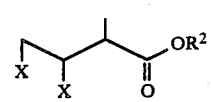

(III)

where X is chlorine or bromine, is dehydrohalogenated by reaction with a solution of an alkali metal hydroxide in an alcohol $R^2OH$, where $R^2$ has the above meaning, or in a mixture of water and an alcohol $R^2OH$.

It was surprising that the halogen addition can be carried out with very good yields and high selectivity even in the absence of inert solvents, since, for similar halogenation reactions, the presence of inert solvents, preferably halohydrocarbons, is generally stipulated (cf. European Patent 31,932 and Organikum, 11th Edition, VEB Deutscher Verlag der Wissenschaften, Berlin, 1972).

It was not to be expected that it would be possible to carry out the dehydrohalogenation of the 2-methyl-3,4-dihalobutyrates of the formula III with excellent yields using alkali metal hydroxides instead of the substantially more expensive alkali metal alcoholates required according to the prior art, since water is liberated in the dehydrohalogenation with an alkali metal hydroxide and it is well known that carboxylate esters of lower alcohols are hydrolyzed smoothly and irreversibly to the corresponding carboxylate salts in aqueous alcoholic media in the presence of alkalis. In contrast, the novel dehydrohalogenation can even be carried out with aqueous alkali metal hydroxide solution.

A further disadvantage of the process disclosed in the above publication (loc. cit.) is that this process does not give sterically pure γ-halotiglates but E/Z isomer mixtures containing a substantial amount of the Z isomer.

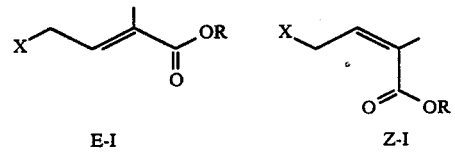

E-I      Z-I

However, a very pure ethyl E-γ-halotiglate isomer is required for the preparation of ethyl β-apo-8'-carotenate.

The novel process gives crude γ-halotiglates as E/Z isomer mixtures having a Z content of about 25–50% in excellent yield and good chemical purity.

Instead of being carried out as a Wittig reaction, a large number of reactions in polyene chemistry are preferably carried out by the Horner-Wittig reaction, which takes place under milder conditions; i.e. instead of the halotiglates being reacted with triphenylphosphine and an acid to give the phosphonium salts and the latter then being reacted with a strong base to give the corresponding ylides, the said halotiglates are reacted with a trialkyl phosphite to give the corresponding phosphonates, which are then reacted with the formyl group of the second component in the presence of a base.

We have found, surprisingly, that substantial isomerization in the direction of the required E isomers takes place in the conversion of alkyl γ-halotiglates by the Michaelis-Arbusow reaction (cf. Houben-Weyl, 12/1, page 434 and loc. cit. 5/1d, page 128) into the alkyl O,O-dialkyl-γ-phosphonotiglates required for the Horner-Wittig reactions. Starting from ethyl γ-chlorotiglate with an E/Z isomer ratio of 1.7:1, the corresponding phosphonate with an E/Z isomer ratio of from 7:1 to 8:1 can be isolated in good yields.

This result is all the more surprising since, when methyl 4-bromo-3-methylcrotonate is reacted with triethyl phosphite by the method known from the literature and under completely comparable reaction conditions, the corresponding methyl O,O-diethyl-4-phosphono-3-methylcrotonate could be obtained only in the form of an E/Z isomer mixture in a ratio of 3:2 (cf. J. Chem. Soc. C (1968), page 1991 and J. Chem. Soc. C (1966), page 2163).

The thermal isomerization found increases the value of the phosphonates as building blocks for the preparation of polyenes by the Horner-Wittig reaction. This reaction is known to take place stereoselectively with regard to the newly formed double bond (Chem. Rev. 1974, page 92, and Houben-Weyl 5/1d, page 129), so that, because of their high E content, the use of phosphonates prepared in this manner would logically be expected to give a high yield of the desired (all-E)-polyenes.

Another, industrially very relevant improvement of the process can be achieved by the use of γ-bromotiglates instead of the conventional γ-chlorotiglates. With these bromine compounds, phosphonate formation takes place at as low as from 70° C. to 100° C. and takes only from 1.5 to 2 hours. The trialkyl phosphite is used in an excess of from 10 to 60%. These reaction conditions result in suppression of the formation of a lactone from the Z isomer, which takes place as a side reaction in the analogous reaction of γ-chlorotiglates, and the yield of the desired product is therefore further increased.

In addition, the use of γ-bromotiglates results in the liberation of ethyl bromide, which has a higher boiling point (38° C.) and is therefore technically substantially easier to handle than ethyl chloride (13° C.). In fact, ethyl chloride has to be collected in cooled solvents, owing to its low boiling point, and the solutions are generally incinerated. Ethyl bromide, on the other hand, can be collected cleanly as such and hence put to further use.

The further isomerization of the resulting E/Z phosphonate mixtures can be carried out in a simple manner, without significant decomposition, by heating the crude products obtained after the low boilers have been distilled off. Distillation gives the desired phosphonates in yields of from 86 to 89% and with an E/Z isomer ratio of from 7:1 to 8:1.

It is particularly advantageous that the γ-bromotiglates obtained in the dehydrohalogenation of the 2-methyl-3,4-dibromobutyrates can be reacted, without purification, with trialkyl phosphites in the desired manner to give phosphonates, without losses of yield similar to those encountered in the reaction of the bromotiglates purified by distillation.

The fact that the purification at the γ-bromotiglate stage can be dispensed with is of course advantageous in terms of process engineering and furthermore has a favourable effect on the total yield of phosphonate, based on the 2-methylbutenoate used. The yield over three stages is thus from 77 to 80% (i.e. about 90-95% per stage), which is noteworthy considering that such reactive compounds are used.

The present invention therefore also relates to a process for the preparation of O,O-dialkyl-γ-phosphonotiglates of the general formula IV

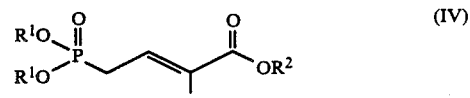
(IV)

where $R^1$ is alkyl of 1 to 4 carbon atoms and $R^2$ is alkyl of 1 to 3 carbon atoms, preferably ethyl, wherein an alkyl γ-halotiglate prepared as described above and of the general formula I

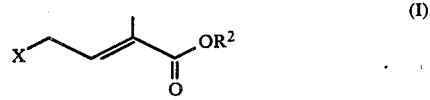
(I)

where X is Cl or Br, preferably Br, and $R^2$ has the above meaning, is reacted with a trialkyl phosphite of the general formula V

(V)

where $R^1$ has the above meaning, and the resulting E/Z-O,O-dialkyl-γ-phosphonotiglate is subjected to thermal isomerization to give the desired O,O-dialkyl-γ-phosphonotiglate having a high E content.

The ethyl O,O-dialkyl-γ-phosphonotiglates of the formula IV which are required for the preparation of the desired compound ethyl β-apo-8′-carotenate have not yet been described in the literature. The methyl O,O-dialkyl-γ-phosphonotiglates (cf. J. Chem. Soc. C (1968), pages 1997-2006, especially 2005) and a general formula in DE 32 44 272 which, in addition to numerous other compounds, also embraces the O,O-dialkyl-γ-phosphonotiglates of the formula IV, without further information about these compounds being given, are all that is known.

For the novel halogenation of the 2-methyl-but-3-enoates of the formula II, these compounds are generally initially taken and from 1.0 to 1.1 equivalents of the halogen are introduced at from about −40° to +20° C., preferably from −10° to 0° C., in about 0.5-2 hours, preferably 1 hour. Chlorine is passed in gaseous form into the reaction mixture, whereas bromine is added in liquid form. Surprisingly, this procedure gives the dihalides of the formula III, in particular the dibromides of the formula III, in excellent yields and purity.

The crude dihalides can be purified by distillation; however, this is not absolutely essential since they can be used directly in the form of crude products in the subsequent stage.

The novel dehydrohalogenation of the 2-methyl-3,4-dihalobutyrates of the formula III can be carried out in various embodiments.

For example, from 1.0 to 1.1 equivalents of the solid alkali metal hydroxide are dissolved in the alcohol corresponding to the ester radical $R^2$, and this solution is run into the crude or distilled dihalide of the formula III, in the absence of a solvent, in the course of from 0.5 to 1.5 hours. The reaction temperature is kept at from about $+20°$ to $-20°$ C., temperatures of from about $0°$ to $-5°$ C. being particularly suitable.

Alternatively, it is also possible to use an aqueous solution of the alkali metal hydroxide. In this procedure, the alcohol corresponding to the ester radical $R^2$ has to be added as a solubilizer. Either a mixture of aqueous hydroxide solution and alcohol is run into the dihalide initially taken without a solvent, or the initially taken dihalide is diluted with the relevant alcohol, and the aqueous hydroxide solution is run in. The reaction conditions stated above with regard to metering of the hydroxide, the reaction time and the reaction temperature also apply to these variants.

This dehydrohalogenation process gives crude γ-halotiglates in the form of E/Z isomer mixtures having a Z content of about 25–50% in excellent yield and good chemical purity.

The crude products can be purified by distillation. On the other hand, they are sufficiently pure to allow them to be used directly in the subsequent stage where further processing is carried out; this applies both when distilled dihalides are used in the dehydrohalogenation and to crude, unpurified dihalides.

The resulting γ-halotiglates can, if desired, be converted by a Michaelis-Arbusow reaction (Houben-Weyl, 12/1, page 434, and 5/1d, page 128) into the alkyl O,O-dialkyl-γ-phosphonotiglates of the formula IV which are desirable for Horner-Wittig reactions.

For this purpose, the γ-halotiglate is added dropwise to a boiling trialkyl phosphite, and the mixture is heated until educt is no longer detectable. It has proven advantageous for the trialkyl phosphite to be initially taken in an excess of about 10γ60%. The pure phosphonates can be isolated by distillation. Surprisingly, we have found that, when E/Z isomer mixtures of the γ-halotiglates are used, substantial isomerization in the direction of the desired E isomer takes place under the reaction conditions themselves.

Further isomerization of the resulting E/Z phosphonate isomer mixtures can be carried out in a simple manner, without significant decomposition occurring, by heating the crude products obtained after the low boilers have been distilled off. Distillation gives the phosphonates of the formula I in yields of from 86 to 89% and with an E/Z isomer ratio of from 7:1 to 8:1.

With the aid of the novel process, it is possible to prepare the O,O-dialkyl-γ-phosphonotiglates of the general formula IV which are particularly suitable as $C_5$ building blocks for numerous reactions in polyene chemistry, in particular the ethyl O,O-dialkyl-γ-phosphonotiglates which have not yet been described as such and are important for the preparation of the valuable compound ethyl β-apo-8'-carotenate, in a technically simple and cheap manner in excellent yield and essentially in the form of the E isomer required for further reaction. In the novel process, the halogenation and the dehydrohalogenation can be carried out in the same reaction vessel and without any intermediate isolation. Even when 3 reaction stages are carried out here without intermediate purification, the phosphonates of the formula IV are obtained in a form which is pure according to gas chromatography and in total yields of from 77 to 80% over 3 stages, which is very surprising for such highly reactive compounds. Compared with the corresponding triarylphosphonium salts previously used for such reactions, the technical advantage that, being liquids, they are substantially easier to handle.

EXAMPLE 1

(a) Ethyl γ-bromotiglate 640 g of ethyl 2-methyl-but-3-enoate (96% pure, corresponding to 4.80 moles) were initially taken at $-25°$ C. 800 g (5.0 moles) of bromine were run in at this temperature in the course of 1 hour (h). Stirring was continued for a further 30 minutes (min) and the temperature was allowed to increase to $-5°$ C. in this time.

A solution of 200 g (5.0 moles) of solid sodium hydroxide in 2 l of ethanol was then added at an internal temperature from $-5°$ to $0°$ C. in the course of 1 h, stirring was once again continued for 30 minutes, the reaction mixture was poured onto 5 l of dilute sulfuric acid (about 1–2 g of concentrated $H_2SO_4$ per l of water) and the organic phase was separated off. The aqueous phase was extracted twice with methylene chloride. The combined organic phases were dried over sodium sulfate and evaporated down in a rotary evaporator.

1,089 g of crude ethyl γ-bromotiglate were obtained.

According to NMR analysis, the product contained 28.8% by weight of ethyl Z-γ-bromotiglate and 53.6% by weight of ethyl E-γ-bromotiglate.

E:Z=1.9:1.

Total content of ethyl γ-bromotiglate: 82.4% by weight, corresponding to a yield of 90.3% of theory (based on ethyl 2-methyl-but-3-enoate used).

(b) Ethyl O,O-diethyl-γ-phosphonotiglate 200 g of the crude ethyl γ-bromotiglate obtained as described in (a), corresponding to 164.8 g (0.8 mole) of the pure substance and having a E/Z isomer ratio of about 1.9 : 1, were added dropwise in the course of 30 minutes to 192.5 g (1.16 moles) of triethyl phosphite at 70° C., while stirring, the temperature increasing to 102° C. The reaction was complete after stirring had been carried out for 80 minutes under reflux. The volatile components were distilled off at 100° C. and under 10 mbar, and the resulting crude product (E/Z isomer ratio 2 : 1 according to GC) was heated at 160° C. for 90 minutes.

Distillation over a short Vigreux column gave 182.6 g (yield 86.4%) of ethyl O,O-diethyl γ-phosphonotiglate having an E/Z isomer ratio of 7.7:1.

Bp. 101°–105° C./0.06 mmHg

EXAMPLE 2

Ethyl γ-bromotiglate 640 g of ethyl 2-methyl-but-3-enoate (97% pure, corresponding to 4.85 moles) were initially taken at $-30°$ C. 800 g (5.0 moles) of bromine were run in at from $-40°$ to $-30°$ C. in the course of 1 h. The reaction mixture was stirred for 30 minutes without cooling and was then diluted with 1.5 l of ethanol. 398 g of a 51.25% strength aqueous sodium hydroxide solution (corresponding to 5.10 moles of sodium hydroxide) were run in at $-5°$ C. in the course of 1 h. Stirring was continued for 15 minutes without cooling, and the mixture was then poured onto a solution of 12 g of concentrated sulfuric acid in 6 l of water. The organic phase was separated off and the aqueous phase was extracted with twice 500 ml of methylene chloride. The combined organic phases were dried over sodium sulfate and evaporated down in a rotary evaporator.

1,054 g of crude ethyl γ-bromotiglate were obtained. According to NMR analysis, the product contained 29.1% by weight of ethyl Z-γ-bromotiglate and 56.0% by weight of ethyl E-γ-bromotiglate.

E:Z ratio = 1.92:1.

Total content of ethyl γ-bromotiglate: 85.1% by weight, corresponding to a yield of 89.3% of theory (based on ethyl 2-methyl-but-3-enoate used).

EXAMPLE 3

(a) Ethyl 2-methyl-3,4-dibromobutyrate 128 g of ethyl 2-methyl-but-3-enoate (98% pure, corresponding to 0.97 mole) were initially taken. 160 g (1 mole) of bromine were run in at −20° C. in the course of 1 h. The mixture was allowed to reach room temperature (RT). Investigation of the crude product (287 g) by gas chromatography showed that a very pure ethyl 2-methyl-3,4-dibromobutyrate had been obtained (purity of the crude product 98–99%).

The crude product can be purified by distillation at 85°–88° C./0.4 mbar to give a purity of 100% according to GC.

(b) A solution of 11.8 g (0.295 mole) of sodium hydroxide in 130 ml of ethanol was run into 85.1 g of the crude product obtained in 3a, at an internal temperature of from −4° to 0° C., in the course of 30 minutes. Thereafter, stirring was continued for a further 30 minutes and the mixture was poured onto dilute hydrochloric acid and extracted three times with methylene chloride. The combined organic phases were dried over sodium sulfate and evaporated down in a rotary evaporator. The residue was distilled over a bridge at 63°–70° C./0.4 mbar; 56.4 g of γ-bromotiglate having a E/Z ratio of about 3:1 were obtained.

(c) 76.6 g (0.266 mole) of the distilled ethyl 2-methyl-3,4-dibromobutyrate obtained as described in Example 3a were reacted with a solution of 10.7 g (0.268 mole) of sodium hydroxide in 120 ml of ethanol similarly to Example 3b). After working up and distillation, 51.7 g of γ-bromotiglate having a E/Z ratio of about 3:1 were obtained.

EXAMPLE 4

(a) Ethyl 2-methyl-3,4-dichlorobutyrate 107.5 g of ethyl 2-methyl-3-butyrate (98% pure, corresponding to 0.823 mole) were initially taken in the absence of a solvent. 62.1 g (0.875 mole) of chlorine were introduced in gaseous form at from −10° to 0° C. in the course of 2 h with thorough stirring. The mixture was allowed to reach room temperature and the crude product was purified by distillation under reduced pressure. 120.4 g (73.5% of theory) of ethyl 2-methyl-3,4-dichlorobutyrate distilled over in the form of a diastereomer mixture in the range from 65° to 79° C. under 0.4 mbar.

(b) Ethyl γ-chlorotiglate 300 g of ethyl 2-methyl-3,4-dichlorobutyrate (94.9% pure, corresponding to 1.43 moles) were initially taken at +5° C. A solution of 60.5 g (1.51 moles) of sodium hydroxide in 600 ml of ethanol was run in at this temperature in the course of 1 h. Stirring was continued for 15 minutes and the mixture was poured onto 1 N hydrochloric acid and extracted three times with diethyl ether. The combined organic phases were dried over sodium sulfate and evaporated down in a rotary evaporator. The residue was purified by distillation under reduced pressure. 215.2 g of a mixture which contained 40.9% of ethyl Z-γ-chlorotiglate and 57.7% of ethyl E-γ-chlorotiglate distilled over at from 69° to 79° C. under 2 mbar.

E:Z = 1.4:1.

Total yield of ethyl γ-chlorotiglate: 91.3% of theory. O,O-diethyl-γ-phosphonotiglate from Z-chlorotiglate 22.12 g (133.1 millimoles) of triethyl phosphite were refluxed, and 19.91 g (122.4 millimoles) of ethyl chlorotiglate having a E/Z isomer ratio of 1:26 were added dropwise in the course of 1 hour. After refluxing had been carried out for 8 h, educt was no longer detectable by gas chromatography. The E/Z isomer ratio was almost 1:1. Further refluxing shifted it to 7.7:1.

By distillation over a short Vigreux column, it was possible to isolate 13.4 g (41.4% yield) of phosphonate.

EXAMPLE 5

O,O-diethyl γ-phosphonotiglate from an E/Z-chlorotiglate mixture 221.42 g (1.33 moles) of triethyl phosphite were refluxed, and 206.56 g of ethyl chlorotiglate (95% pure, corresponding to 1.21 moles) having an E/Z isomer ratio of 1.4:1 were added dropwise in the course of 2 h. Stirring was continued until gas was no longer evolved.

Distillation over a 10 cm packed column gave 217.0 g (68.0% yield) of phosphonate having an E/Z isomer ratio of 7.6:1.

EXAMPLE 7

Ethyl γ-bromotiglate from ethyl 2-methyl-but-3-enoate 800 g (5.0 moles) of bromine were added to 640 g of ethyl 2-methyl-but-3-enoate (97% pure, corresponding to 4.85 moles) at 0° C. in the course of 1 h. Thereafter, stirring was continued for 30 minutes at 0° C., the mixture was diluted with 2 l of ethanol and 410 g of a 51.2% strength by weight aqueous sodium hydroxide solution (5.25 moles of NaOH were then added at 0° C. in the course of 1 h. Stirring was then continued for 15 minutes at 0° C. and the mixture was poured onto a solution of 6 g of concentrated sulfuric acid in 6 l of water. When phase separation was complete, the organic phase was separated off, the aqueous phase was extracted once with 1 l of toluene and the two organic phases were then combined.

The combined organic phases of two identical batches were evaporated down using a laboratory Sambay evaporator at 60° C./50 mbar. 2,055 g of a bottom product containing 38.1% of Z isomer and 53.9% of E isomer were obtained.

This corresponded to an average yield of 94.2% of theory of ethyl γ-bromotiglate per batch.

We claim:

1. A process for the preparation of an O,O-dialkyl-γ-phosphonotiglate of formula (IV):

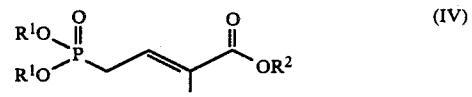

wherein $R^1$ is alkyl of 1 to 4 carbon atoms and $R^2$ is alkyl of 1 to 3 carbon atoms, said phosphonotiglate having a high E isomer content, comprising:

(a) reacting 2-methyl-but-3-enoate of formula (II):

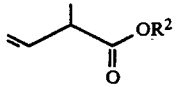

with Cl or Br in the absence of a solvent;

(b) dehydrohalogenating the resulting 2-methyl-but-3-4-dihalobutyrate of the formula:

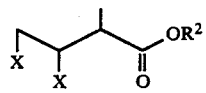

wherein X is Cl or Br in a solution of an alkali metal hydroxide in an alcohol $R^2OH$, wherein $R^2$ has the meaning stated above, or in a mixture of water with an alcohol $R^2OH$;

(c) reacting the resulting γ-chloro or γ-bromotiglate having a certain E/Z isomer ratio of the formula (I):

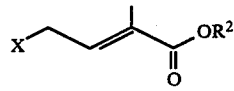

wherein X and $R^2$ have the meanings stated above with a trialkylphosphite of formula (V):

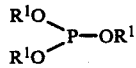

wherein $R^1$ has the meaning stated above; and (d) subjecting the resulting O,O-dialkyl-γ-phosphonotiglate to thermal isomerization conditions to give a phosphonotiglate product having a high E isomer content.

2. A process as claimed in claim 1, wherein, in reaction step (a), the 2-methyl-but-3-enoate of the formula II is reacted with bromine, (b) the resulting 2-methyl-3,4-dibromobutyrate of the formula III is dehydrohalogenated and (c) the resulting γ-bromotiglate is reacted with a trialkyl phosphite of the formula V.

3. A process for the preparation of an O,O-dialkyl-γ-phosphonotiglate of formula (IV)

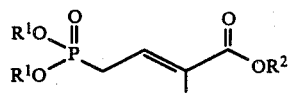

wherein $R^1$ is alkyl of 1 to 4 carbon atoms and $R^2$ is alkyl of 1 to 3 carbon atoms, comprising:

reacting an alkyl γ-halotiglate of formula (I):

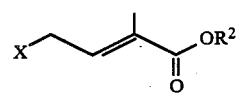

wherein X is Cl or Br and $R^2$ has the meaning stated above with a trialkylphosphate of formula (V):

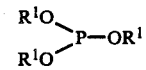

wherein $R^1$ has the meaning stated above; and then subjecting the resulting O,O-dialkyl-γ-phosphonotiglate having an E/Z-ratio to thermal isomerization thereby effecting an increase in the E/Z ratio of the product O,O-dialkyl-γ-phosphonotiglate such that the compound has a high E isomer content 4. The process for the preparation of an O,O-dialkyl-γ-phosphonotiglate having a high E content as claimed in claim 3, wherein, in stage (b), a dibromo compound of the formula III in the form of the resulting crude product is dehydrohalogenated.

5. The process for the preparation of an O,O-dialkyl-γ-phosphonotiglate having a high E content as claimed in claim 3, wherein, in stage (c), the γ-bromotiglate of the formula I, in the form of the resulting crude product, is reacted with a trialkyl phosphite of the formula V.

* * * * *